(12) United States Patent
Rodríguez García et al.

(10) Patent No.: US 12,313,614 B2
(45) Date of Patent: May 27, 2025

(54) METHOD FOR IDENTIFYING THE QUALITY OF A LIQUID PHARMACEUTICAL PRODUCT

(71) Applicant: Laura Rodríguez García, Potsdam (DE)

(72) Inventors: Laura Rodríguez García, Potsdam (DE); David Mainka, Potsdam (DE)

( * ) Notice: Subject to any disclaimer, the term of this patent is extended or adjusted under 35 U.S.C. 154(b) by 86 days.

(21) Appl. No.: 17/774,708

(22) PCT Filed: Jan. 28, 2020

(86) PCT No.: PCT/EP2020/052043
§ 371 (c)(1),
(2) Date: May 5, 2022

(87) PCT Pub. No.: WO2021/144038
PCT Pub. Date: Jul. 22, 2021

(65) Prior Publication Data
US 2022/0397562 A1    Dec. 15, 2022

(30) Foreign Application Priority Data
Jan. 17, 2020 (DE) .................... 10 2020 101 082.6

(51) Int. Cl.
*G01N 33/15* (2006.01)
*G01N 21/13* (2006.01)
(Continued)

(52) U.S. Cl.
CPC ............. *G01N 33/15* (2013.01); *G01N 21/13* (2013.01); *G01N 21/3577* (2013.01);
(Continued)

(58) Field of Classification Search
CPC .... G01N 33/15; G01N 21/13; G01N 21/3577; G01N 21/359; G01N 21/65; G01N 2021/135; G01N 2021/651
See application file for complete search history.

(56) References Cited

U.S. PATENT DOCUMENTS

| | | | |
|---|---|---|---|
| 5,187,368 A | 2/1993 | Galante et al. | |
| 5,510,621 A | 4/1996 | Goldman | |
| | (Continued) | | |

FOREIGN PATENT DOCUMENTS

| | | |
|---|---|---|
| CN | 1789981 | 6/2006 |
| EP | 1 635 698 | 8/2013 |
| | (Continued) | |

OTHER PUBLICATIONS

Broad et al., Non-invasive determination of ethanol, propylene glycol and water in a multi-component pharmaceutical oral liquid by direct measurement through amber plastic bottles using Fourier transform near-infrared spectroscopy, Analyst, Oct. 17, 2000, vol. 125, pp. 2054-2058. (Year: 201).*

(Continued)

*Primary Examiner* — Edwin C Gunberg
*Assistant Examiner* — Richard O Toohey
(74) *Attorney, Agent, or Firm* — Dicke, Billig & Czaja, PLLC (57) ABSTRACT

A method and a system for identifying the quality of a liquid pharmaceutical product as described. The method comprises providing a liquid pharmaceutical product in a sealed container and arranging the sealed container such that the liquid pharmaceutical product forms a sample layer in a first portion of the sealed container. The method further comprises directing a light beam through the sample layer and measuring a spectrum of the sample layer. The spectrum is chosen from the group of a NIR spectrum or a Raman (Continued)

spectrum. The method further comprises identifying the quality of the liquid pharmaceutical product by comparing the spectrum with a reference spectrum corresponding to an expected pharmaceutical product.

26 Claims, 6 Drawing Sheets

(51) Int. Cl.
    *G01N 21/3577*     (2014.01)
    *G01N 21/359*     (2014.01)
    *G01N 21/65*     (2006.01)

(52) U.S. Cl.
    CPC ........... *G01N 21/359* (2013.01); *G01N 21/65* (2013.01); *G01N 2021/135* (2013.01)

(56) References Cited

U.S. PATENT DOCUMENTS

| | | | |
|---|---|---|---|
| 5,859,703 A * | 1/1999 | Aldridge | G01N 21/51 356/326 |
| 10,261,030 B2 | 4/2019 | Angermund et al. | |
| 10,612,993 B2 | 4/2020 | Maurischat | |
| 2014/0319356 A1 | 10/2014 | Sartorius et al. | |
| 2015/0022802 A1 | 1/2015 | Long et al. | |
| 2019/0285471 A1 | 9/2019 | Milo et al. | |

FOREIGN PATENT DOCUMENTS

| | | |
|---|---|---|
| JP | H08-210973 | 8/1996 |
| JP | H09-236553 | 9/1997 |
| JP | 2006266948 | 10/2006 |
| JP | 2006-527358 | 11/2006 |
| JP | 2018-509606 | 4/2018 |
| JP | 2018-517912 | 7/2018 |
| WO | 2004/107969 | 12/2004 |

OTHER PUBLICATIONS

Cui et al., Aluminium foil as a potential substrate for ATRFTIR, transflection FTIR or Raman spectrochemical analysis of biological specimens, Anal. Methods, 2016, Vo.8, pp. 481-487. (Year: 2016).*
International Search Report and Written Opinion in PCT/EP2020/052043.

* cited by examiner

METHOD FOR IDENTIFYING THE QUALITY OF A LIQUID PHARMACEUTICAL PRODUCT

CROSS-REFERENCE TO RELATED APPLICATIONS

This Utility Patent Application claims priority under 35 U.S.C. § 371 to International Application Serial No. PCT/EP2020/052043, filed Jan. 28, 2020, which claims priority to DE 10 2020 101 082.6, filed Jan. 17, 2020, both of which are incorporated herein by reference in its entirety.

Aspects of the present application generally relate to a method for identifying the quality of a liquid pharmaceutical product. The method is, in particular, carried out with a pharmaceutical product in a sealed container. Aspects of the present application also relate to a corresponding system for identifying the quality of a liquid pharmaceutical product.

TECHNICAL BACKGROUND

Pharmaceutical products serve to cure or prevent diseases. Incorrect production or storage of pharmaceutical products can result in the absence of healing effects, or may even have a harmful effect on the organism to which the pharmaceutical products are applied.

It is therefore of importance to determine the quality of pharmaceutical products. Such determination can, for example, be done by evaluating spectroscopic measurements of a sample of the pharmaceutical product placed in a sample container.

Many of the above approaches require sample preparation or result in the destruction of the sample. Moreover, those approaches often require an analytical laboratory as well as trained, highly specialized people, for example, to evaluate the spectra.

SUMMARY OF THE INVENTION

The present invention intends to overcome at least some of the above problems. The object is solved by the method according to claim 1, and by the system according to claim 25. Further advantages, features, aspects and details of the invention are evident from the dependent claims, the description and the drawings.

The disclosed method comprises providing a liquid pharmaceutical product in a sealed container. The sealed container is arranged such that the liquid pharmaceutical product forms a sample layer in a first portion of sealed container. A light beam is directed through the sample layer and a spectrum of the sample layer is measured. The spectrum may be a NIR spectrum or a Raman spectrum. By comparing the spectrum with a reference spectrum the quality of the liquid pharmaceutical product may be identified. The reference spectrum may correspond to an expected pharmaceutical product.

The method according to the disclosure aims to spectroscopically identify the quality of a liquid pharmaceutical product which is provided in a sealed container, i.e. in the liquid pharmaceutical product's closed (primary) packaging. A determination of the pharmaceutical product in its sealed container allows a fast and easy measurement without the need to open the container or to prepare or extract samples. Furthermore, the method allows a determination of the quality of a sterile pharmaceutical product without loss of sterility.

BRIEF DESCRIPTION OF FIGURES

The invention will be better understood by reference to the following description of embodiments of the invention taken in conjunction with the accompanying drawings, wherein.

DETAILED DESCRIPTION

Figure 1:
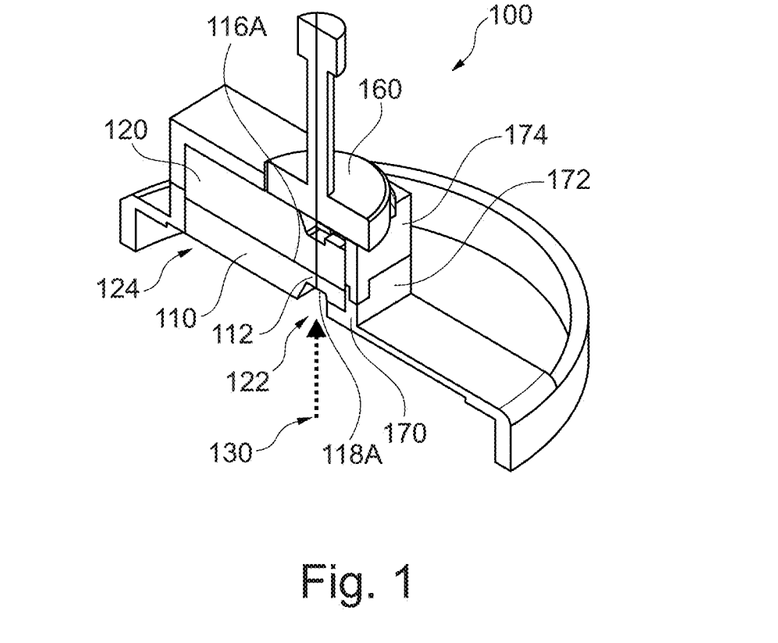
FIG. 1 shows schematically a system used in a method according to an embodiment of the disclosure.

FIG. 1 shows a system 100 for identifying the quality of a liquid pharmaceutical product 110. The system 100 may be adapted for carrying out a method for identifying the quality of a liquid pharmaceutical product 110 as disclosed herein.

The liquid pharmaceutical product 110 is provided in a sealed container 120. The liquid pharmaceutical product 110 may be a ready-to-use liquid like an injection fluid. The sealed container 120 corresponds to the closed (primary) packaging of the liquid pharmaceutical product 110. The sealed container 120 may comprise a first portion 122 and a second portion 124. The first portion 122 may have a smaller cross-section than the second portion 124. In FIG. 1, the sealed container is bottle-shaped and comprises a bottleneck portion and a bottle-body portion. The sealed container 120 may also have other shapes, for example the sealed container may be a syringe or an infusion bag filled with the liquid pharmaceutical product.

The sealed container 120 is arranged such that the liquid pharmaceutical product forms a sample layer 112. The sample layer 112 may be located in the first portion 122 of the sealed container 120. The second portion 124 may comprise a bulk area 114 of the liquid pharmaceutical product 110.

A thickness of the sample layer 112 may be configured to provide an optical path length qualified to measure a spectrum as further described below. The thickness of the sample layer 112 may be dependent on the expected pharmaceutical product and/or the aimed spectrum. For example, the thickness of the sample layer may be about 0.5 to 2 mm for measuring a transmission-reflection NIR spectrum for a liquid pharmaceutical product that is expected to contain an aqueous solvent.

In FIG. 1, the sealed container 120 is arranged such that a longitudinal axis of the sealed container is perpendicular to the gravitation axis. Such arrangement may provide the sample layer 112.

Figure 9:
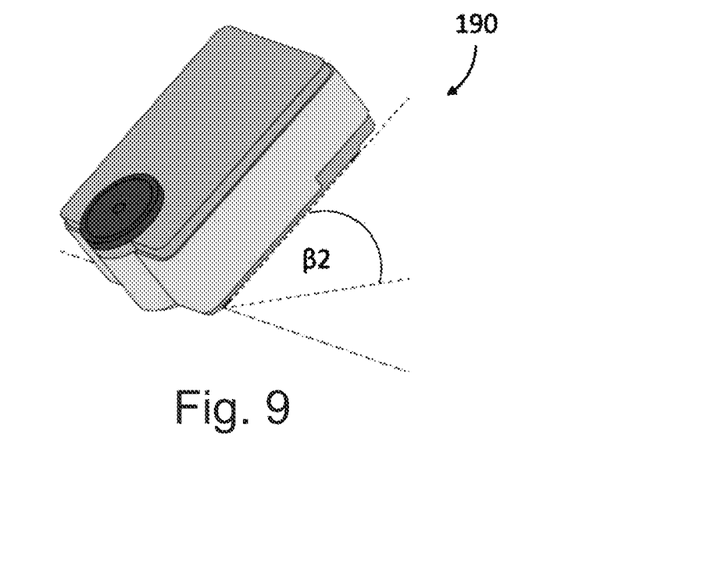
FIGS. 9 and 10 shows schematically an inclined measurement unit used in a method according to an embodiment of the disclosure.

As shown in FIG. 1, a light beam 130 is directed through the sample layer 112 in the first portion 122 of the sealed container 120. The light beam 130 may be emitted by a light source (not shown). The light beam 130 may be directed through a measurement window 132 (shown in FIGS. 2, 3 and 10, for example) in direction of the sample layer 112. The light beam 130 may be detected by a detector (not shown). The light source and the detector may be part of a measurement unit 190, for example, a spectrometer (shown in FIGS. 9 and 10, for example). The measurement unit may also comprise the measurement window 132.

As shown in FIG. 1, the system 100 may further comprise a reflector 160. The reflector 160 may be arranged at a site of the sealed container being opposite to the site of the sealed container 120 where the light source and/or the detector are provided. The reflector 160 may reflect the light beam 130 after the light beam 130 has penetrated the sample layer 112 a first time such that the light beam 130 penetrates the sample layer 112 a second time (i.e. transmission-reflection). Twice passing the sample layer 112 results in an optical path length that is twice as long as the thickness d of the sample layer 112.

In FIG. 1, the sample layer 112 is located in the bottle-neck portion as the first portion 122 of the sealed container 120. Forming the sample layer 112 in a bottle-neck portion may be advantageous as the bottle-neck portion usually does not comprise a label which could prevent the light beam from penetrating the sample layer 112.

The arrangement of the sealed container may be provided by a sample holder 170. The sample holder 170 may be configured to hold the sealed container 120. In particular, the sample holder 170 may be configured to hold the sealed container in a predefined position with respect to the light beam 130 and/or the reflector 160. The sample holder 170 may comprise the reflector as for example shown in FIG. 8. The sample holder 170 may be configured to hold the sealed container 120 such that the liquid pharmaceutical product 110 forms the sample layer 112 in the first portion 122 of the sealed container 120.

In FIG. 1, the sample holder comprises a first sample-holder component 172 and a second sample-holder component 174. The first sample-holder 172 component may be configured to provide a fixed position of the sealed container 120 with respect to the light beam 130 and/or with respect to the measurement unit 190. The second sample-holder component 174 may be configured to ensure a fixed position of the sealed container 120 with respect to the reflector 160.

Directing the light beam 130 through the sample layer 112 allows measurement of a spectrum of the sample layer 112. The light beam 130 may be a NIR light beam or a laser beam exciting inelastic scattering of photons. The measured spectrum may be a NIR spectrum or a Raman spectrum. FIGS. 4 to 7 show NIR transmission-reflection spectra that may result from the disclosed method according to the described embodiments.

For identifying the quality of the liquid pharmaceutical product 110 the measured spectrum may be compared with a reference spectrum. The reference spectrum may correspond to an expected pharmaceutical product that is expected to be equal to the liquid pharmaceutical product 110. Identifying the quality of the liquid pharmaceutical product 110 may be based on chemometrics. For example, a spectral distance (e.g. Euclidean, Mahalanobis) between the spectrum and the reference spectrum may be determined. The spectral distance may be used to determine the similarity between the measured spectrum and the reference within a given error limit.

It may be recognized that the measured spectrum may also comprise signals originating from the sealed container. However, the sealed container for a specific liquid pharmaceutical product are usually standardized. The sealed container of the liquid pharmaceutical product and the expected pharmaceutical product and also their signals may therefore be identical. Those signals may be minimalized or eliminated for example by chemometrics.

As described above, in FIG. 1 the sealed container 120 is arranged such that the longitudinal axis of the sealed container is perpendicular to the gravitation axis. However, depending, for example, on the measured spectrum, the filling state of the sealed container 120 and/or the absorption coefficient of the liquid pharmaceutical product 110, such arrangement may not provide a sample layer 112. For example, such arrangement may form a layer of the liquid pharmaceutical product being not suitable as a sample layer 112. For example, the thickness d, i.e. the distance between two opposing interfaces of the layer, may be too large to allow the measurement of the spectrum.

Figure 2:
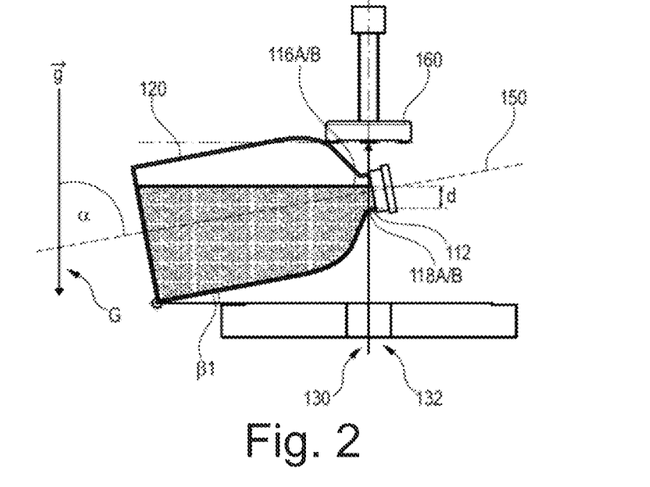
FIG. 2 shows schematically a system with an inclined sealed container used in a method according to an embodiment of the disclosure.
Figure 3:
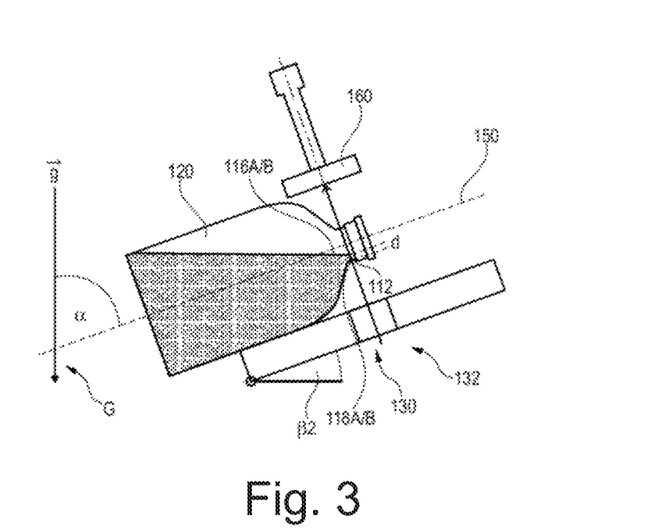
FIG. 3 shows schematically a measurement system with an inclined measurement unit used in a method according to an embodiment of the disclosure.

In the latter case, the sealed container may be arranged such that an acute container angle is provided between the longitudinal axis of the sealed container and the gravitation axis. The container angle $\alpha$ is illustrated in FIGS. 2 and 3. The container angle $\alpha$ is provided between the gravitation axis G and the longitudinal axis 150 of the sealed container 120. In FIGS. 2 and 3 the container angle $\alpha$ is an acute angle, wherein the first portion 122 is lifted with respect to the second portion 124.

Arranging the sealed container with an acute container angle $\alpha$ may decrease the thickness of liquid pharmaceutical product 110 in the first portion such that the sample layer 112 is formed with a thickness d. The thickness d of the sample layer is defined in the same direction as the light beam 130. The thickness d of the sample layer corresponds to the distance between a first interface 116A and a second interface 118A of the sample layer 112. In FIGS. 2 and 3 the first interface 116A corresponds to a gas-liquid interface 116B, wherein the second interface 118A corresponds to a container-liquid interface 118B. However, the first interface 116A may also comprise a container-liquid interface.

As shown in FIGS. 2 and 3 the sealed container may be arranged such that the first interface 116B of the sample layer 112 is inclined relative to the second interface 118B of the sample layer.

As shown in FIG. 2, the container angle $\alpha$ may be realized by inclining only the sealed container 120 with respect to the measurement unit 190. For example, the sample holder 170 (not shown) may be configured to hold the sealed container 120 in a first angle $\beta 1$ with respect to the measurement unit 190 such that the container angle $\alpha$ is provided.

Figure 4:
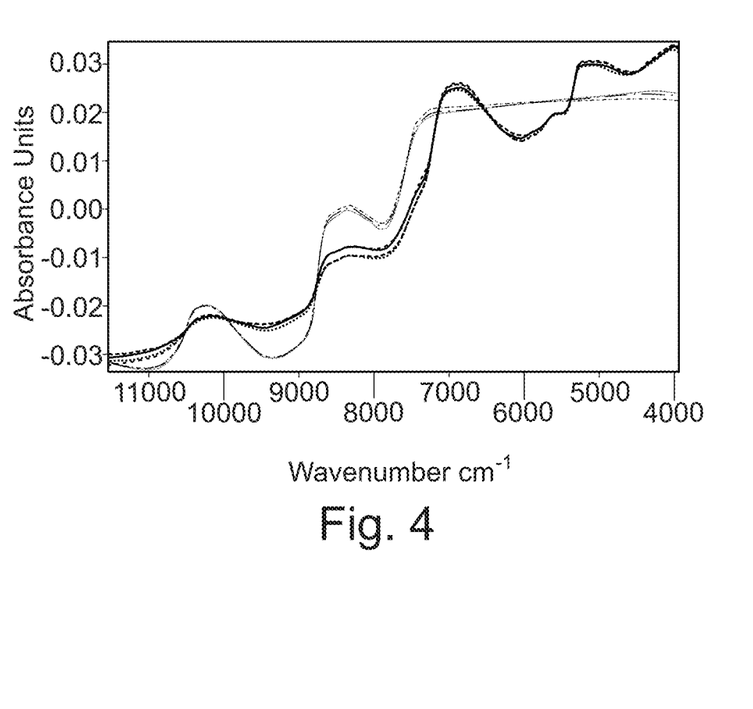
FIGS. 4 to 7 shows exemplary spectra resulting from methods according to embodiments of the disclosure.

FIG. 4 shows an exemplary transmission-reflection NIR spectra (SNV: Standard Normal Variate) measured with a FT-NIR spectrometer. The grey spectra relate to Onkotrone as 10 mg as liquid pharmaceutical product, wherein the sealed container was arranged with a container angle of 90°. The black spectra relate to Onkotrone as 10 mg as liquid pharmaceutical product, wherein the sealed container was arranged with a container angle of 84°. The inclination changed the thickness of the sample layer. It may be recognized that the black spectra exhibit signals, for example, in a range between 5500 and 6500 cm$^{-1}$ which are not present in the grey spectra. Those signals may be necessary or helpful to identify the quality of the liquid pharmaceutical product.

As shown in FIG. 3, the container angle $\alpha$ may also be realized by inclining the whole measurement unit 190 together with the sealed container 120. For example, an inclination unit (not shown) may be provided under the measurement unit 190. The inclination unit may comprise an inclination table 180 (for example shown in FIG. 10). The inclination unit may be configured to provide the container angle $\alpha$. For example, the inclination unit may lift on site of the measurement unit 190 with respect to another site of the measurement unit 190. For example, a measurement unit angle β2 may be provided between the measurement unit and a plane on which the measurement unit stands, for example, a table or the ground. Such arrangement is exemplarily illustrated in FIGS. 9 and 10.

Figure 5:
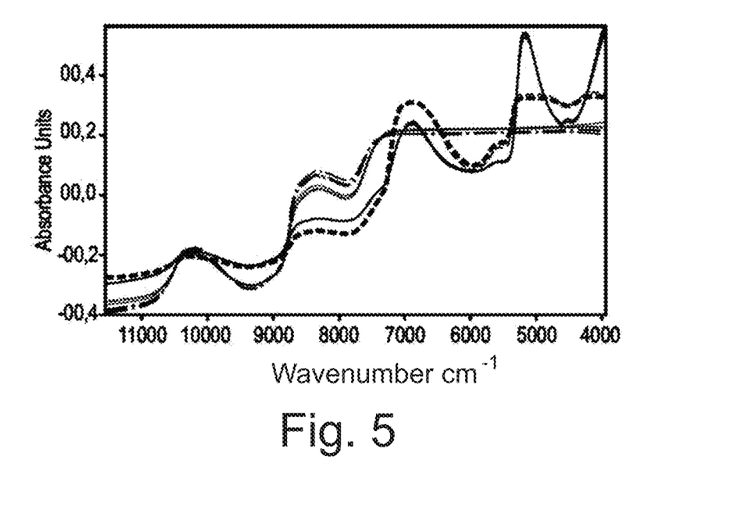

FIG. 5 shows exemplary transmission-reflection NIR spectra (SNV) measured with a FT-NIR spectrometer. The spectra relate to Avastin 400 mg (dashed lines and dash dots) and Perjeta 420 mg (solid lines and dotted lines) as liquid pharmaceutical products. For each of the liquid pharmaceutical products the FT-NIR spectrometer was one time inclined for the measurement (dashed lines and solid lines) and one time not (dash-dots and dotted lines). The inclination changed the thickness of the sample layer. It may be recognized that the spectra measured with an inclined FT-NIR spectrometer exhibit signals, for example, in a range between 4000 and 7000 cm$^{-1}$ which are not present in spectra where the FT-NIR spectrometer was not inclined.

Figure 6:
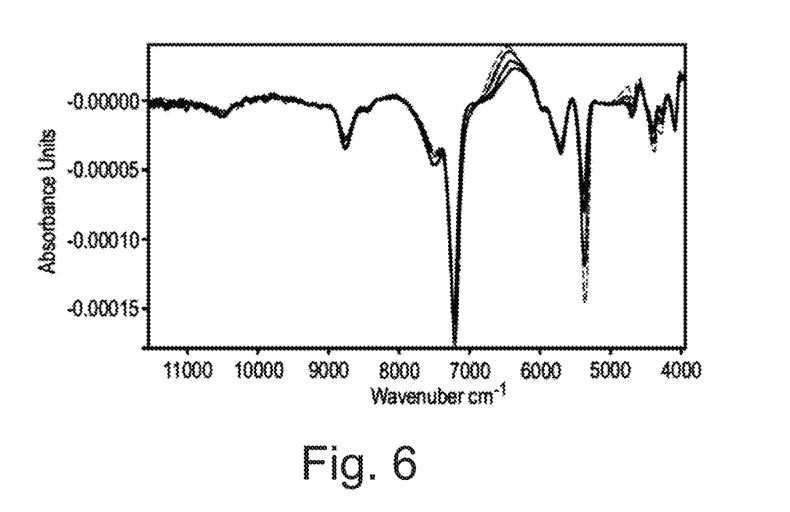

FIG. 6 shows exemplary transmission-reflection NIR spectra (SNV and first derivative with 25 smoothing points) measured with a FT-NIR spectrometer. The spectra relate to Avastin 100 mg as liquid pharmaceutical product. For each measurement the FT-NIR spectrometer inclined with a different measurement unit angle β2, i.e. 21°, 22°, 23°, 24° and 25°. In this example, the best signals were achieved with the 25° which provided the smallest thickness of the sample layer (cf. dashed line).

Figure 7:
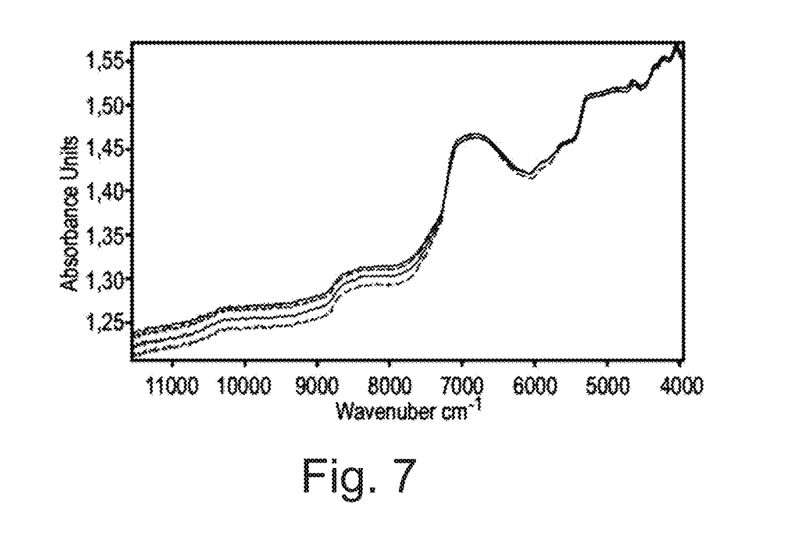

FIG. 7 shows exemplary transmission-reflection NIR spectra (raw data) measured with a FT-NIR spectrometer. The spectra relate to Eylea 4 mg as liquid pharmaceutical products. For the measurements the FT-NIR spectrometer was inclined with β2 being 9° (solid line) or with β2 being 10° (dashed line). The sample layer was measured two times at both measurement unit angles. It may be recognized that the two spectra with β2=10° are more closely together than the spectra with β2=9°. In this example, the best reproducibility was achieved with the lower value for β2 which provided a larger thickness of the sample layer. The better reproducibility may be attributed to a less sensitivity according to interface effects like air bubbles.

As can be seen from the examples, it may be advantageous to provide a different container angle α for each liquid pharmaceutical product.

Figure 10:
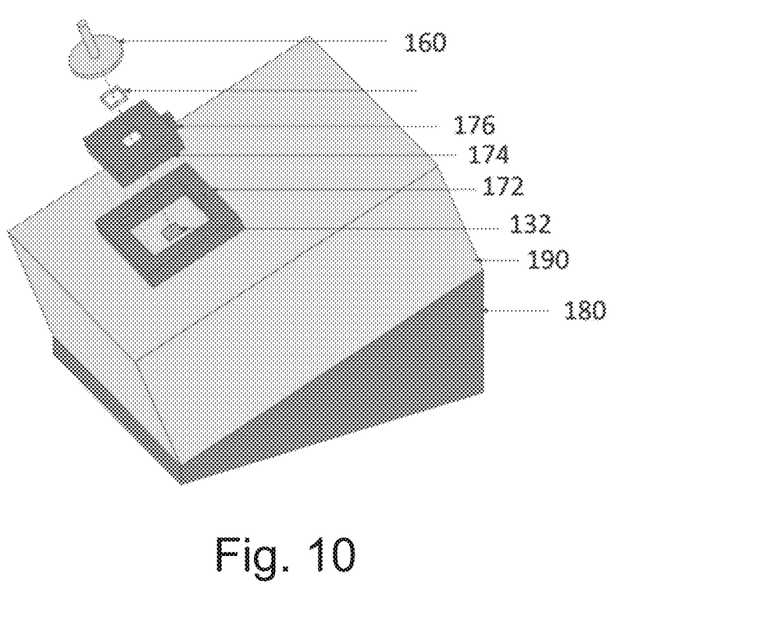

The inclination unit 180 may be adjustable to adjust the container angle α. As shown in FIG. 10, the system 100 may comprise an electronical chip 176. The electronical chip 176 may be configured to communicate with the inclination unit 180. The electronical chip 176 may be configured to induce an action of the inclination unit 180, for example, such that the inclination unit automatically adjusts the container angle α.

Description of Further Aspects:

Next, various more general aspects of the invention are defined in more detail. Each aspect so defined may be combined with any other embodiment or with any other aspect(s) unless clearly indicated to the contrary. Reference signs referring to the Figures are for illustration only, but are not intended to limit the respective aspect(s) to the embodiments shown in the Figures.

Next, aspects relating to the liquid pharmaceutical product in the sealed container are described.

According to an aspect, the liquid pharmaceutical product is a ready-to-use liquid. For example, the liquid pharmaceutical product may be an injection fluid, a vaccine or eye drops. For example, the liquid pharmaceutical product may be Avastin 100 mg, Avastin 400 mg, Cellcristin, Epirubicin, Eylea, 5-FU Baxter, Jevtana, Herceptin, Lucentis, MabThera, Neotaxan, Opdivo, Paclitaxel, Perjeta, RoActemra, Soliris or Truxima.

According to an aspect, the sealed container is an unopened primary packing of the liquid pharmaceutical product. For example, the sealed container may be a sterile primary packaging.

An advantage of this aspect is that the quality of a pharmaceutical product may be determined without contamination or loss of sterility of the pharmaceutical product.

For example, the sealed container may be a capsule, a bottle, a syringe or an infusion bag. An example of a bottle is for example an injection vial. Injection vials are used in many areas of medicine and in chemical laboratories and may contain liquids like solutions or suspensions. An injection vial may be closed with a septum or with an injection plug.

According to an aspect, the sealed container has a capacity of 0.05 to 1000 ml. The sealed container may also have a capacity of 0.3 ml to 500 ml. The sealed container may also have a capacity of 0.5 to 200 ml. According to an aspect, the sealed container is a small container having a capacity of 0.05 to 10 ml. The small container may also have a capacity of 0.2 to 5 ml. According to another aspect, the sealed container is a large container having a capacity of 100 to 1000 ml. The large container may also have a capacity of 250 to 1000 ml.

According to one aspect, the sealed container is a single-dose container. According to another aspect, the sealed container is a multiple-dose container.

According to one aspect, the sealed container comprises glass, plastic and/or gelatine.

According to one aspect, the sealed container is non-opaque. For example, the sealed container may be a transparent container.

According to one aspect, the first portion of the sealed container is non-opaque. For example, the first portion may be a transparent. The first portion may not comprise a label, for example, comprising paper.

An advantage of the above aspects is that only a little or nothing of the spectral range of the light beam is absorbed by the container.

Next, aspects relating to the arrangement of the sealed container and the formed sample layer are described.

According to an aspect, the sealed container is arranged such that a thickness of the liquid pharmaceutical product varies between the bulk area and the sample layer. The thickness of the of the liquid pharmaceutical product is defined in the same direction as the light beam. The thickness of the of the liquid pharmaceutical product comprises the thickness of the sample layer and/or the bulk area. The bulk area describes the area of the liquid pharmaceutical product containing the remaining volume of the liquid pharmaceutical product, i.e. the volume of the liquid pharmaceutical product minus the volume of the sample layer. The bulk area may describe the area containing the main volume of the liquid pharmaceutical product.

According to an aspect, the sealed container is arranged such that the sample layer has a smaller thickness than a bulk area of the liquid pharmaceutical product. For example, the thickness of the liquid pharmaceutical product may decrease continuously between the bulk area and the sample layer.

According to another aspect, the sealed container is arranged such that the sample layer has a larger thickness than the bulk area of the liquid pharmaceutical product. For example, if there is only a small amount of liquid pharmaceutical product in the sealed container, it may be advantageous to arrange the sealed container such that a larger or even the entire amount of liquid pharmaceutical product is provided in the first portion of the sealed container to form the sample layer.

The thickness of the sample layer may be dependent on the kind different spectral range of the light beam.

The thickness of the sample layer may be dependent on the kind of measurement, for example whether a reflection, emission, transmission or a transmission-reflection spectrum of the sample layer is measured. For example, for reflection spectrum the sample layer does not need to be penetrated by the light beam. For a transmission spectrum the sample layer needs to be penetrated by the light beam once. For a transmission-reflection the sample layer needs to be penetrated by the light beam twice, i.e. in addition to the transmission also by the reflected light beam. For example, an optical path length of a sample layer having a certain thickness is larger for a transmission-reflection measurement than for transmission measurement.

According to an aspect, the sample layer is configured to provide an optical path length qualified to measure a transmission or transmission-reflection NIR spectrum for the sample layer of the liquid pharmaceutical product in the sealed container.

The thickness of the sample layer may be dependent on the expected pharmaceutical product. For example, an expected pharmaceutical product using an alcohol as a solvent may have another upper and/or lower limit for the thickness of the sample layer than an expected pharmaceutical product using water or an oil as a solvent, for example due to different absorption coefficients.

According to an aspect, the sealed container is arranged such that the thickness of the sample layer is not larger than 10 mm. The sealed container may be arranged such that the thickness of the sample layer is not larger than 5 mm. The sealed container may be arranged such that the thickness of the sample layer is not larger than 2 mm. The sealed container may be arranged such that the thickness of the sample layer is not larger than 1 mm.

According to an aspect, the sealed container is arranged such that the thickness of the sample layer provides an optical path length being not larger than 20 mm. The sealed container may be arranged such that the thickness of the sample layer provides an optical path length being not larger than 10 mm. The sealed container may be arranged such that the thickness of the sample layer provides an optical path length being not larger than 5 mm.

An advantage of the two previous aspects is that the quality of the measured spectra may be increased. The thickness of the sample layer may be a parameter influencing the quality of the measured spectrum. As the proposed method comprises the measurement of a transmission or a transmission-reflection spectrum of the sample layer, the thickness of the sample layer may not be too large in order to allow the light beam to penetrate the sample layer at least once (for transmission) or at least twice (for transmission-reflection).

According to an aspect, the sealed container is arranged such that the thickness of the sample layer is not smaller than 0.1 mm. The sealed container may be arranged such that the thickness of the sample layer is not smaller than 0.2 mm. The sealed container may be arranged such that the thickness of the sample layer is not smaller than 0.5 mm.

According to an aspect, the sealed container is arranged such that the thickness of the sample layer provides an optical path length being not smaller than 3 mm. The sealed container may be arranged such that the thickness of the sample layer provides an optical path length being not smaller than 1 mm. The sealed container may be arranged such that the thickness of the sample layer provides an optical path length being not smaller than 0.5 mm.

An advantage of the previous aspects is that the probability of reproducible measurements is increased. A too small thickness of the sample layer may be difficult to reproduce for several measurements, for example to adhesion or surface effects. For example, bubbles occurring mainly on the gas-liquid interface of the sample layer may influence the measurements. The thinner the sample layer, the larger the influence of air bubbles might be.

According to an aspect, arranging the sealed container comprises providing a container angle $\alpha$. The container angle may be defined as an angle between a longitudinal axis of the sealed container and the gravitation axis. For example, the longitudinal axis of a bottle-shaped sealed container passes a bottom surface of the body-shaped portion and the (sealed) opening of the bottle-neck portion. The container angle may be a perpendicular angle, i.e. the longitudinal axis may be perpendicular to the gravitation axis. For example, a bottle-shaped container lying on a side wall on the ground comprises a perpendicular container angle. The container angle may also be an acute angle. For example, a bottle-shaped container with a lifted bottle-neck portion with respect to the bottle-body portion comprises an acute container angle. A zero angle, i.e. a longitudinal axis being parallel to the gravitation axis is not considered a container angle. For example, a bottle-shaped container standing on a bottom surface does not exhibit a container angle.

According to one aspect, the providing the container angle comprises choosing the container angle in dependence of the expected pharmaceutical product. For example, the container angle for a liquid pharmaceutical product which is expected to be Onkotrone may be always 84°.

An advantage of this aspect is that, an improvement in the reproducibility of the measurements can be achieved. Normally, the sealed containers and filling levels of a specific liquid pharmaceutical product are always the same. A specific container angle for the specific liquid pharmaceutical product can ensure to have for each measurement a sample layer with the same thickness and, thus, better comparable measurement results.

According to one aspect, the container angle is 90° or less. The container angle may be 85° or less. The container angle may be larger 80° or less.

According to one aspect, the container angle is 10° or more. The container angle may be 20° or more. The container angle may be 40° or more.

According to one aspect, the sealed container is inclined relative to the gravitation axis in order to provide the container angle. For example, the sealed container may be inclined by a sample holder providing the container angle.

According to one aspect, measuring the spectrum of the sample layer is provided by a measuring system. The measuring system may comprise a light source and a detector. For example, the measurement unit may be embodied as spectrometer. According to one aspect, the measurement unit is inclined relative to the gravitation axis in order to provide the container angle. For example, the sealed container may be fixed to the measurement unit and one side of the measurement unit may be lifted with respect to another side of the measurement unit. The measurement unit may provide measurement unit angle $\beta 2$ with the gravitation axis.

An advantage of this aspect is that, the distance between reflector and sample layer is not reduced (cf. for example FIG. 2 in comparison with FIG. 3). In addition, the light beam may be able to penetrate the sample unhindered without any risk of being interrupted, for example by the lid of a bottle-shaped sealed container.

According to one aspect, the sample layer comprises a gas-liquid interface and a container-liquid interface. The container-liquid interface may be opposite the gas-liquid interface. The distance between the gas-liquid interface and a container-liquid interface may define the thickness of the sample layer. The container-liquid interface and the gas-liquid interface may be penetrated by the light beam.

The container-liquid interface and the gas-liquid interface describe idealized flat surfaces. For example, curvatures of the container-liquid interface due to the shape of the container may be neglected for the definition of the container-liquid interface. The container-liquid interface may be assumed to be a tangential plane at the lowest point of a curved interface between container and liquid. For example, curvatures of the gas-liquid interface due to surface tension or edge effects caused by adhesion to the container wall are neglected for the definition of the gas-liquid interface. The gas-liquid interface may be assumed to be a tangential plane at the lowest point of a curved interface between gas and liquid.

According to another aspect, the sample layer comprises two container-liquid interfaces. The two container-liquid interfaces may be opposite to each other. The distance between the two container-liquid interfaces may define the thickness of the sample layer. The two container-liquid interfaces may be penetrated by the light beam. The two container-liquid interfaces may describe idealized flat surfaces as described in more detail above.

For example, a sample layer comprising two container-liquid interfaces may be provided by a cross section of the first portion of the sealed container. For example, a sealed container may comprise a first portion having a first cross-section. A length of first cross-section in direction of the light beam may be dimensioned such that the length corresponds to the thickness of the sample layer. For example, the sample layer may be formed by a bottle-neck portion of a bottle-shaped container.

According to one aspect, the light beam may be directed such that it penetrates the container-liquid interface and/or the gas-liquid interface perpendicularly. For a perpendicular penetration a main direction of the light beam may be approximately equivalent to the direction of a surface normal of the respective interface. The container-liquid interface and/or the gas-liquid interface may be perpendicular to the light beam.

According to one aspect, the sealed container is arranged such that a container-liquid interface is non-perpendicular to the gravitation axis. As the gas-liquid interface is perpendicular to the gravitation axis, the gas-liquid interface may be inclined relative to the container-liquid interface. The gas-liquid interface my be inclined such that the gas-liquid interface and the container-liquid interface approach in direction of the first portion of the sealed container.

An advantage of this aspect is that, relatively independently of a shape or dimension of the sealed container, any thickness of the sample layer may be provided in the first portion of the sealed container. For example, even for a sealed container with a large capacity and containing a large amount of liquid pharmaceutical product, a first portion with a sample layer may be realized, wherein the sample layer is thin enough to allow measurement of transmission or transmission-reflection.

According to one aspect, the light beam is directed through the sample layer in a direction that is non-parallel to the gravitation axis. In particular, the light beam may be directed through the gas-liquid interface of the sample layer in a direction that is non-parallel to the gravitation axis. The light beam may be directed through the sample layer such that the NIR light beam penetrates the gas-liquid interface non-perpendicularly.

According to one aspect, the sealed container is arranged such that the gas-liquid interface is non-parallel to the reflector.

An advantage of the above aspects is that, the light beam (comprising the reflected light beam) strikes the gas-liquid interface being naturally perpendicular to the gravitation axis at a non-perpendicular angle of incidence which may improve the quality of the spectrum.

However, according to another aspect, the light beam is directed through the sample layer in a direction that is substantially parallel to the gravitation axis. The light beam may be directed through the sample layer such that the light beam penetrates the gas-liquid interface substantially perpendicular.

According to one aspect, arranging the sealed container is provided by a sample holder holding the sealed container. The sample holder may be configured to hold the sealed container in a predefined container angle. The sample holder may be configured to hold the sealed container in a predefined position with respect to the light beam.

According to one aspect, the sample holder is characteristic for the expected pharmaceutical product. The sample holder may also be chosen in dependence of the shape of the sealed container or the filling state.

An advantage of the above aspects is that, an improvement in the reproducibility of the measurements can be achieved. In addition, the comparability with the reference spectrum may be enhanced. For example, the expected pharmaceutical product, which is usually provided in an analogous container as the liquid pharmaceutical product to be tested, may be measured with a sample holder providing penetration of the light beam at a specific position of the analogous container. A sample layer of the expected pharmaceutical product may exhibit a certain thickness at the specific position, for example due to a container angle provided by the sample holder. The liquid pharmaceutical product to be identified may be measured with the same sample holder such that the light beam penetrates the sample layer of the liquid pharmaceutical product having the same thickness as the sample layer of the expected pharmaceutical product.

According to one aspect, the sample holder comprises a shaped holder surface corresponding to a container surface of the sealed container. The shaped holder surface may be configured to prevent the container from being displaced. For example, the shaped holder surface may comprise at least one projection corresponding to a depression in the container surface.

Figure 8:
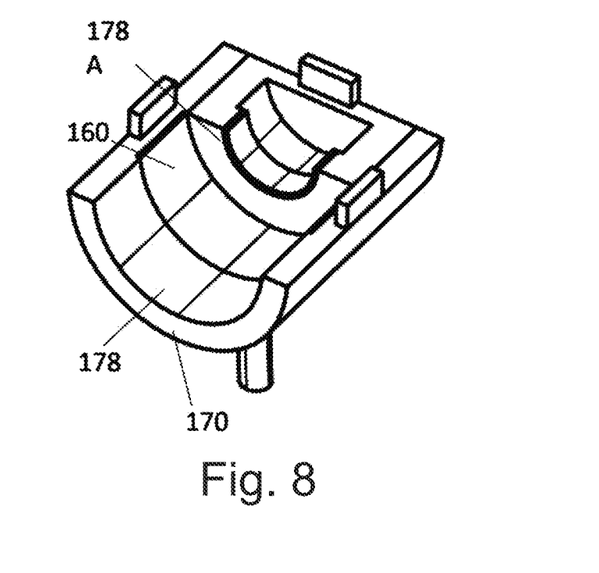
FIG. 8 shows schematically a sample holder used in a method according to an embodiment of the disclosure.

For example, FIG. 8 illustrates a sample holder 170 (or a at least a part of it) having a shaped holder surface 178 with one projection 178A. The shaped holder surface 178 may correspond to a sealed container being bottle-shaped. The sample holder in FIG. 8 also comprises the reflector 160, wherein the reflector comprises a shaped reflecting surface.

The shaped holder surface may also comprise two, three or more projections corresponding to two, three or more depression in the container surface. The shaped holder surface may comprise a curved surface corresponding to a curved container surface.

The sample holder may comprise one, two or more sample-holder components. For example, the sample holder may comprise a first sample holder component. The first sample-holder component may be configured to ensure a reproducible position of the sealed container with respect to the light beam and/or with respect to the measuring system, for example, the spectrometer. For example, the first component may have a first shaped surface corresponding to a shaped measurement-system surface. The first sample-holder component may be configured to house the sealed container. For example, the first component may have a second shaped surface, opposite to the first shaped surface, corresponding to a first container surface. The first sample-holder component may also be configured to house a further component housing the sealed container.

According to one aspect, the sample holder may comprise the reflector. For example, the shaped holder surface may comprise the reflector.

According to one aspect, the sample holder may comprise a second sample holder component. For example, the second sample holder component may be configured to ensure a reproducible position of the sealed container with respect to the reflector. The second sample holder component may comprise the reflector.

Next, aspects relating to measurement are described.

According to one aspect, the light beam is embodied as a near-infrared (NIR) light beam. According to one aspect, measuring a spectrum of the sample layer may comprise measuring a NIR spectrum of the sample layer.

The NIR range lies between the red visible light and the mid-infrared (MIR). The border between the MIR and NIR lies where the IR radiation is no longer able to penetrate glass. The spectral range for NIR comprises wave length from 780 to 2500 nm or wave numbers from 13,000 to 4,000 $cm^{-1}$.

An advantage of this aspect is that, NIR can be measured fast, easy, cost-effective and without destruction of the sample. NIR can also be measured in a glass container. In addition, NIR exhibits higher energy and lower absorption coefficients than MIR. In particular, water is a less strong absorber in the NIR than in the MIR. Consequently, NIR allows penetration of sample layers having a relatively large thickness.

NIR spectroscopy may provide wide absorption bands which may overlap. However, the NIR spectrum may provide a number of chemical and physical information of the sample layer. Such information may be obtained by using mathematical and/or statistical methods. Those methods are usually called chemometrics. Chemometrics describe mathematical-statistical methods, which are used for the evaluation of physical-chemical analysis data.

According to one aspect, measuring a spectrum of the sample layer may comprise measuring a transmission NIR spectrum of the sample layer. For measuring a NIR transmission spectrum the absorbance of the liquid pharmaceutical product may be measured.

An advantage of this aspect is that the optical path length is relatively small because the sample layer has to be penetrated only once. A transmission NIR spectrum may be advantageous for liquid pharmaceutical products exhibiting relatively large absorption coefficients. A transmission NIR spectrum may be advantageous for liquid pharmaceutical products being provided with a relatively large thickness of the sample layer.

According to one aspect, measuring a spectrum of the sample layer may comprise measuring a reflection NIR spectrum of the sample layer. For measuring a NIR reflection spectrum the diffuse reflection of the light beam at the liquid pharmaceutical product may be measured.

An advantage of this aspect is that liquid pharmaceutical products exhibiting absorption coefficients being too large for a transmission of the light beam may also be measured. For example, non-opaque liquids may be measured by reflection NIR.

According to one aspect, measuring a spectrum of the sample layer may comprise measuring a transmission-reflection NIR spectrum of the sample layer. For measuring a NIR transmission spectrum the absorbance of the liquid pharmaceutical product may be measured. According to one aspect, measuring a transmission-reflection NIR spectrum of the sample layer comprises reflecting the light beam after the light beam has penetrated the sample layer a first time such that the light beam penetrates the sample layer a second time.

According to one aspect, reflecting the light beam is provided by a reflector. The reflector may be arranged at a site of the sealed container being opposite to the site of the sealed container where a source of the light beam is provided.

According to one aspect, the reflector has a curved reflecting surface. An advantage of this aspect is that a loss of intensity of the reflected light beam may be minimized. A loss of intensity may be due to refraction on interfaces, for example.

According to one aspect, the reflector has a rough reflecting surface. An advantage of this aspect is that diffuse reflection of the light beam may be provided.

According to one aspect, a distance between the reflector and the sample layer is not larger than 30 mm. The distance between the reflector and the sample layer may be not larger than 25 mm. The distance between the reflector and the sample layer may be not larger than 20 mm.

According to one aspect, a distance between the reflector and the sample layer is not smaller than 15 mm. The distance between the reflector and the sample layer may be not smaller than 10 mm. The distance between the reflector and the sample layer may be not smaller than 8 mm. The distance between the reflector and the sample layer may be not smaller than 4 mm.

Next, aspects relating to identifying the quality of the liquid pharmaceutical product are described.

According to one aspect, comparing the spectrum with a reference spectrum comprises a pretreating the spectrum. A pretreatment may be mathematical operations correcting the measured spectrum. The pretreatment may correct the spectrum of unwanted influences. The pretreatment may also highlight properties of interest. The pretreatment may comprise scattering correction methods. For example, normalization may be used to prepare the spectrum. The pretreatment may comprise spectra derivatives. A derivative of a spectrum may be determined by the Savitzky-Golay algorithm.

According to one aspect, identifying the quality of the liquid pharmaceutical product comprises chemometrically evaluating the spectrum. For example, a spectral distance between the spectrum and the reference spectrum may be determined. Various methods are known for calculating the spectral distance. For example, the Euclidean distance can be determined. Alternatively, or in addition, it may be intended to determine the Mahalanobis distance. The spectral distance may be used to determine the similarity of the spectra to be compared within a given error limit.

According to an aspect, the method further comprises quantifying an active ingredient of the liquid pharmaceutical product. For example, an active ingredient may comprise characteristic absorption centres in a transmission or transmission-reflection NIR. A measured NIR spectrum may provide information about the absorption centres in the sample layer having a certain thickness. The grade of transmission is dependent on the amount of absorption centres. Accordingly, with the thickness of the sample layer and the grade of transmission, quantifying an active ingredient may be realized.

According to one aspect, the light beam is embodied as a laser beam exciting inelastic scattering of photons. According to one aspect, measuring a spectrum of the sample layer may comprise measuring a Raman spectrum of the sample layer.

According to one aspect, the Raman spectrum may be a transmission Raman spectrum.

An advantage of these aspects is that results of Raman spectroscopy do not face interference from water molecules, due to the fact that water molecules have permanent dipole moments, i.e. water molecules do not exhibit Raman scattering. Raman spectroscopy may be used to obtain similar and/or complementary information as in NIR spectroscopy.

According to a further aspect, a system for identifying the quality of a liquid pharmaceutical product is provided. The system comprises a sample holder. The sample holder may be configured to hold a sealed container. As described above, the sealed container contains a liquid pharmaceutical product. The sample holder may be configured to hold the sealed container such that the liquid pharmaceutical product forms a sample layer in a first portion of the sealed container.

The system further comprises a measurement unit. The measurement unit comprises a light source and a detector. The measurement unit may be configured to direct a light beam from the light source through the sample layer. The measurement unit may be further configured to measure a spectrum of the sample layer. The spectrum may be a NIR spectrum or a Raman spectrum.

The system may further comprise a reflector as described above. The reflector may be arranged on an opposite site of the sealed container than the NIR source and the detector.

The system may further comprise an inclination unit. The inclination unit may be configured to provide the container angle as described above. The inclination unit may be embodied as an inclination table configured to lift one side of the measurement unit. The inclination unit may also be attached to or embedded in the sample holder. The inclination unit may be adjustable to adjust the container angle in dependence of the expected pharmaceutical product.

According to one aspect, the system further comprises an electronical chip. For example, the sample holder may comprise the electronical chip. The electronical chip may be configured to induce arrangement of the sealed container with the container angle automatically. For example, a sample holder being characteristic for a certain expected pharmaceutical product, filling state and/or shape of the sealed container may induce the container angle for the expected pharmaceutical product, filling state and/or shape of the sealed container. For example, the electronical chip may communicate with an inclination table configured to lift the measuring system e.g. the spectrometer) on one side.

According to a further aspect, the system described herein is adapted for carrying out the methods according to any of the embodiments and aspects described herein.

It will be appreciated that elements or features shown with any method, system or embodiment herein are exemplary for the specific method or system and may be used on or in combination with other methods or systems disclosed herein.

REFERENCE SIGNS

100 System
110 Liquid pharmaceutical product
112 Sample layer
116A First interface
116B Gas-liquid interface
118A Second interface
118B Container-liquid interface
120 Sealed container
122 First portion
124 Second portion
130 Light beam
132 Measurement window
150 Longitudinal axis
160 Reflector
170 Sample holder
172 First sample holder component
174 Second sample holder component
176 Electronical chip
178 Shaped sample holder surface
178A Projection of sample holder surface
180 Inclination unit
190 Measurement unit
d Thickness of sample layer
G Gravitation axis
$\alpha$ Container angle
$\beta 1$ First angle
$\beta 2$ Measurement unit angle

The invention claimed is:

1. A method for identifying the quality of a liquid pharmaceutical product, comprising:
   providing a liquid pharmaceutical product in a sealed container;
   arranging the sealed container such that the liquid pharmaceutical product forms a sample layer in a first portion of the sealed container;
   directing a light beam through the sample layer;
   measuring a spectrum of the sample layer,
   wherein the spectrum is a NIR spectrum or a Raman spectrum; and
   identifying the quality of the liquid pharmaceutical product by comparing the spectrum with a reference spectrum corresponding to an expected pharmaceutical product; and
   wherein the sample layer comprises a gas-liquid interface and a container-liquid interface penetrated by the NIR light beam;
   wherein the sealed container is arranged such that the gas-liquid interface is inclined relative to the container-liquid interface.

2. The method according to claim 1, wherein the spectrum is a transmission, transmission-reflection or reflection NIR spectrum.

3. The method according to claim 1, wherein the sealed container further comprises a second portion, wherein the first portion has a smaller cross-section than the second portion.

4. The method according to claim 1, wherein the sealed container is bottle-shaped and comprises a bottle-neck portion and a bottle-body portion, wherein the bottle-neck portion comprises the first portion of the sealed container.

5. The method according to claim 1, wherein the sealed container is arranged such that the sample layer has a smaller thickness than a bulk area of the liquid pharmaceutical product.

6. The method according to claim 1, wherein arranging the sealed container comprises providing a container angle between a longitudinal axis of the sealed container and a gravitation axis, wherein the container angle is an acute or perpendicular angle.

7. The method according to claim 6, wherein providing the container angle comprises choosing the container angle in dependence of the expected pharmaceutical product.

8. The method according to claim 6, wherein the container angle is 90 degree or less and/or 10 degree or more.

9. The method according to claim 6, wherein measuring the spectrum of the sample layer is provided by a measuring system comprising a light source and a detector and wherein providing the container angle comprises inclining a measurement system relative to the gravitation axis.

10. The method according to claim 1, wherein the NIR light beam is directed through the sample layer in a direction that is non-parallel to a gravitation axis.

11. The method according to claim 1, wherein arranging the sealed container is provided by a sample holder holding the sealed container.

12. The method according to claim 11, wherein the sample holder comprises a shaped holder surface corresponding to a container surface of the sealed container.

13. The method according to claim 12, wherein the shaped holder surface comprises at least one projection corresponding to a depression in the container surface.

14. The method according to claim 12, wherein the shaped holder surface comprises the reflector.

15. A method for identifying the quality of a liquid pharmaceutical product, comprising:
    providing a liquid pharmaceutical product in a sealed container;
    arranging the sealed container such that the liquid pharmaceutical product forms a sample layer in a first portion of the sealed container;
    directing a light beam through the sample layer;
    measuring a spectrum of the sample layer,
    wherein the spectrum is a NIR spectrum or a Raman spectrum; and
    identifying the quality of the liquid pharmaceutical product by comparing the spectrum with a reference spectrum corresponding to an expected pharmaceutical product;
    wherein the sealed container is arranged such that the sample layer has a smaller thickness than a bulk area of the liquid pharmaceutical product; and
    wherein the sealed container is arranged such that a thickness of the liquid pharmaceutical product decreases continuously between the bulk area and the sample layer.

16. A method for identifying the quality of a liquid pharmaceutical product, comprising:
    providing a liquid pharmaceutical product in a sealed container;
    arranging the sealed container such that the liquid pharmaceutical product forms a sample layer in a first portion of the sealed container;
    directing a light beam through the sample layer;
    measuring a spectrum of the sample layer,
    wherein the spectrum is a NIR spectrum or a Raman spectrum; and
    identifying the quality of the liquid pharmaceutical product by comparing the spectrum with a reference spectrum corresponding to an expected pharmaceutical product; and
    wherein the sample layer comprises a gas-liquid interface and a container-liquid interface penetrated by the NIR light beam;
    wherein the sealed container is arranged such that the gas-liquid interface is inclined relative to the container-liquid interface;
    wherein the sealed container is arranged such that a thickness of the sample layer is not larger than 10 mm and not smaller than 0.1 mm.

17. A method for identifying the quality of a liquid pharmaceutical product, comprising:
    providing a liquid pharmaceutical product in a sealed container;
    arranging the sealed container such that the liquid pharmaceutical product forms a sample layer in a first portion of the sealed container;
    directing a light beam through the sample layer;
    measuring a spectrum of the sample layer,
    wherein the spectrum is a NIR spectrum or a Raman spectrum; and
    identifying the quality of the liquid pharmaceutical product by comparing the spectrum with a reference spectrum corresponding to an expected pharmaceutical product;
    wherein the sample layer comprises a gas-liquid interface and a container-liquid interface penetrated by the NIR light beam; and
    wherein the sealed container is arranged such that the gas-liquid interface is perpendicular to a gravitation axis and the container-liquid interface is non-perpendicular to the gravitation axis.

18. A method for identifying the quality of a liquid pharmaceutical product, comprising:
    providing a liquid pharmaceutical product in a sealed container;
    arranging the sealed container such that the liquid pharmaceutical product forms a sample layer in a first portion of the sealed container;
    directing a light beam through the sample layer;
    measuring a spectrum of the sample layer,
    wherein the spectrum is a NIR spectrum or a Raman spectrum; and
    identifying the quality of the liquid pharmaceutical product by comparing the spectrum with a reference spectrum corresponding to an expected pharmaceutical product; and
    wherein the sealed container is arranged such that a first interface of the sample layer is inclined relative to a second interface of the sample layer, wherein the second interface opposes the first interface.

19. A method for identifying the quality of a liquid pharmaceutical product, comprising:
    providing a liquid pharmaceutical product in a sealed container;
    arranging the sealed container such that the liquid pharmaceutical product forms a sample layer in a first portion of the sealed container;
    directing a light beam through the sample layer;
    measuring a spectrum of the sample layer,
    wherein the spectrum is a NIR spectrum or a Raman spectrum; and
    identifying the quality of the liquid pharmaceutical product by comparing the spectrum with a reference spectrum corresponding to an expected pharmaceutical product; and wherein the sample layer comprises a gas-liquid interface and a container-liquid interface penetrated by the NIR light beam;

wherein the sealed container is arranged such that the gas-liquid interface is inclined relative to the container-liquid interface;

reflecting the light beam after the light beam has penetrated the sample layer a first time such that the light beam penetrates the sample layer a second time.

20. The method according to claim 19, wherein reflecting the light beam is provided by a reflector arranged on an opposite site of the sealed container than a light source for the light beam.

21. The method according to claim 20, wherein the reflector has a curved and/or rough reflecting surface.

22. A method for identifying the quality of a liquid pharmaceutical product, comprising:

providing a liquid pharmaceutical product in a sealed container;

arranging the sealed container such that the liquid pharmaceutical product forms a sample layer in a first portion of the sealed container;

directing a light beam through the sample layer;

measuring a spectrum of the sample layer, wherein the spectrum is a NIR spectrum or a Raman spectrum; and identifying the quality of the liquid pharmaceutical product by comparing the spectrum with a reference spectrum corresponding to an expected pharmaceutical product; and wherein the NIR light beam is directed through the sample layer such that the NIR light beam penetrates the gas-liquid interface non-perpendicularly.

23. A system for identifying the quality of a liquid pharmaceutical product, comprising:

a sample holder configured to hold a sealed container such that a liquid pharmaceutical product contained in the sealed container forms a sample layer in a first portion of the sealed container; and a measurement unit comprising a light source and a detector, wherein the measurement unit is configured to direct a light beam through the sample layer, and wherein the measurement unit is configured to measure a spectrum of the sample layer, wherein the spectrum is a NIR spectrum or a Raman spectrum; and wherein the sample layer comprises a gas-liquid interface and a container-liquid interface penetrated by the NIR light beam, wherein the sealed container is arranged such that the gas-liquid interface is inclined relative to the container-liquid interface.

24. The system according to claim 23, further comprising:

a reflector, wherein the reflector is arranged on an opposite site of the sealed container than the light source and the detector.

25. The system according to claim 23, further comprising:

an inclination unit configured to provide a container angle between a longitudinal axis of the sealed container and a gravitation axis, wherein the container angle is an acute or perpendicular angle.

26. The system according to claim 23, wherein the inclination unit is adjustable for providing a container angle in dependence of the expected pharmaceutical product.

* * * * *